(12) United States Patent
Chen et al.

(10) Patent No.: US 9,447,437 B2
(45) Date of Patent: Sep. 20, 2016

(54) **GENETICALLY ENGINEERED *TORULOPSIS GLABRATA* WITH ENHANCED EXTRACELLULAR SECRETION OF PYRUVIC ACID**

(71) Applicants: Jian Chen, Wuxi (CN); Hongwei Guo, Wuxi (CN); Jingwen Zhou, Wuxi (CN); Guocheng Du, Wuxi (CN)

(72) Inventors: Jian Chen, Wuxi (CN); Hongwei Guo, Wuxi (CN); Jingwen Zhou, Wuxi (CN); Guocheng Du, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 332 days.

(21) Appl. No.: 14/185,928

(22) Filed: Feb. 21, 2014

(65) Prior Publication Data
US 2015/0176036 A1  Jun. 25, 2015

(30) Foreign Application Priority Data
Dec. 24, 2013  (CN) .......................... 2013 1 0722490

(51) Int. Cl.
| | | |
|---|---|---|
| C12N 1/14 | (2006.01) | |
| C12P 7/40 | (2006.01) | |
| C12N 15/00 | (2006.01) | |
| C07H 21/02 | (2006.01) | |
| C07K 1/00 | (2006.01) | |
| C12N 15/81 | (2006.01) | |
| C12N 1/16 | (2006.01) | |
| C07K 14/195 | (2006.01) | |

(52) U.S. Cl.
CPC ................ *C12P 7/40* (2013.01); *C07K 14/195* (2013.01); *C12N 1/16* (2013.01); *C12N 15/815* (2013.01)

(58) Field of Classification Search
CPC ...... C12N 15/815; C12P 7/40; C07K 14/195
See application file for complete search history.

(56) References Cited

PUBLICATIONS

Branden et al. Introduction to Protein Structure, Garland Publishing Inc., New York, p. 247, 1991.*

* cited by examiner

*Primary Examiner* — Yong Pak
(74) *Attorney, Agent, or Firm* — Lili Chen

(57) ABSTRACT

The present invention provides a genetically engineered *Torulopsis glabrata* with enhanced extracellular secretion of pyruvic acid. *T. glabrata* strain was obtained from China Center for Type Culture Collection with CCTCC No: M202019 and over-expressed the optimized CutA (SEQ ID NO:2) encoding stress protein. Both of the temperature tolerance of *T. glabrata* and extracellular concentration of pyruvate were improved by overexpressing the optimized CutA. The optimum growth temperature of genetically engineered *T. glabrata* was increased too. The present invention can be widely used to increase extracellular levels of pyruvate during the fermentation process.

9 Claims, 3 Drawing Sheets

SEQUENCE LISTING

<160> NUMBER OF SEQ ID NOS: 5

<210> SEQ ID NO 1
<211> LENGTH: 310
<212> TYPE: DNA
<213> ORGANISM: Pyrococcus horikoshii

<400> SEQUENCE: 1

```
atgataatag tttacacgac ttttccggac tgggagagtg ctgagaaagt tgtgaaaact      60
cttttaaaag agaggttgat tgcatgcgca aatttaaggg agcacagggc cttttactgg     120
tgggaaggta agatcgagga agataaagaa gttggagcta tccttaaaac tagggaagat     180
ctgtgggaag aacttaagga aaggataaag gagcttcatc cttacgatgt tccggccata     240
atcaggattg acgttgatga tgttaacgag gattacctca aatggttaat tgaagagacg     300
```
aaaaaatgag                                                                310

<210> SEQ ID NO 2
<211> LENGTH: 310
<212> TYPE: DNA
<213> ORGANISM: Artificial Sequence
<220> FEATURE:
<223> OTHER INFORMATION: Computer generated sequence

<400> SEQUENCE: 2
atgatcatcg tttacactac tttcccagac tgggaatctg ctgaaaaggt tgttaagact    60
ttgttgaagg aaagattgat cgcttgtgct aacttgagag aacacagagc tttctactgg   120
tgggaaggta agatcgaaga agacaaggaa gttggtgcta tcttgaagac tagagaagac   180
ttgtgggaag aattgaagga aagaatcaag gaattgcacc catacgacgt tccagctatc   240
atcagaatcg acgttgacga cgttaacgaa gactacttga agtggttgat cgaagaaact   300
aagaagtaag                                                                310

<210> SEQ ID NO 3
<211> LENGTH: 21
<212> TYPE: DNA
<213> ORGANISM: artificial sequence
<220> FEATURE:
<223> OTHER INFORMATION: Primer sequence

<400> SEQUENCE: 3
ctttcccaga ctgggaatct g                                                    21

<210> SEQ ID NO 4
<211> LENGTH: 19
<212> TYPE: DNA
<213> ORGANISM: Artificial Sequence
<220> FEATURE:
<223> OTHER INFORMATION: Primer sequence

<400> SEQUENCE: 4
ttagtggtgg tggtggtgg                                                       19

<210> SEQ ID NO 5
<211> LENGTH: 1600
<212> TYPE: DNA
<213> ORGANISM: Saccharomyces cerevisae

<400> SEQUENCE: 5
acggtgaaag gtataacagc gagaccgaat gaggtccggt actctgttgt gccaccatcc    60 atttagagc ttggagttaa agttgcccag ggttcaggtg gagcgtacgc agttagcgca   120
atactactta atagagatgc tagaaatgct ttcttgtaat gcatattggg gcggtgttca   180
cttcttcagt aagttgtata gaattaaaaa atcgagacta aacagaaatt cgaaacaag   240 aagataagta tatgtataca agttatttta ctcttttaac tgttttcgtt tccccactct   300
ttcgcaaaaa gaataatttt gtgagtcaaa acagtcgaat tttcttgcac aaaaagtcga   360
tattcttttg tgactctgtg taacttactt tctacagctt tgttactcc acttctctta   420 tatataccca atgattcact cgtaatatat cagaggaacg ttagaatttc tgtattttct   480
caggaatcct acaaaattag aggtgaaatt gatcaggtta aggagcagaa gcccactata   540
taagtaagat gatatcaagc ctagttggat gccttcagga acggcaaata ggatatgtga   600
gcttggcaaa ggggttttga tagagtaaca atagatcctt gctagccaat gcgacgttcc   660

```
tctgtagttt ttaccacagt tttacttaat ttcgtgcttt gtcccttttt ggcaaaaaag    720
tcggataatg tcttcactat atttgtgttt tcgtcttttta ggaaaagcgt actttagtaa    780
actacaaatt tgagctgagc taatttcgga ttagtaaaag atgcaaggaa cagtaaaaat    840
taaaatagcg attgaccgaa atcagtccaa aaattactac aacaagcaaa tccaattaaa    900
aacagtaaaa tactttaagt gcatttaccg ttacgaacaa catatgtcct agttagtata    960
gtagtctact aagtagcaaa aaagtagaaa ctctgtcact ataccagcca tcagttcata   1020
gtaaaacagt aaaaattgta aaaacaagca aaaaaaaaac aagaaggaac aaatgcacca   1080
aactgttgat ctattctgca aaaaaaagta tggtaaattt tttccattat cctggccgct   1140
aatccatatg gaggtgaact tagaacttgc acaaggatgc gatgaatgat aggctttgtg   1200
ctataattaa tgcaggcagg tccgccatgt ccaacacgtt gctggccgca aaacgagtca   1260
atctcactgc tttgccacgc tcatttctcc cccttctgc ccaattaggc gaccctcaca   1320
atgcacatac acatttccca cctctattgg aagggccgt aaatggtaat tcttgggagt   1380
tattcatatt aagtgatctt actatttcct atttcggaaa ttattaaaga caaaaaagct   1440
cattaatggc tttccgtctg tagtgataag tcgccaactc agcctaattt ttcatttctt   1500
taccagatca ggaaaactaa tagtacaaat gagtgtttc tcaagcggaa caccacattt   1560
tgagctaaat ttagattttg gtcaaaataa gaaagatcct                         1600
```

GENETICALLY ENGINEERED *TORULOPSIS GLABRATA* WITH ENHANCED EXTRACELLULAR SECRETION OF PYRUVIC ACID

CROSS-REFERENCES AND RELATED APPLICATIONS

This application claims the benefit of priority to Chinese Application No. 201310722490.1, entitled "A Genetically Engineered *Torulopsis glabrata* with Enhanced Extracellular Secretion of Pyruvic Acid and Its Application", filed Dec. 24, 2013, which is herein incorporated by reference in its entirety.

BACKGROUND OF THE INVENTION

1. Field of the Invention

The present invention relates to the field of metabolic engineering, and more particularly relates to a genetically engineered strain of *Torulopsis glabrata* with enhanced extracellular secretion of pyruvic acid.

2. Description of the Related Art

As one of the important oxo carboxylic acid, pyruvic acid is the precursor of many helpful chemical compounds and plays a key role in bioenergy metabolism. It is also widely used in chemical, pharmaceutical and agrochemical industries and scientific research. Industrial production of pyruvic acid has been achieved through both chemical methods and biological fermentation. With regard to large scale application of the chemical method, high raw material costs and low productivity are limitations. The bio-fermentation process is complex and is easily affected by different growth parameters such as temperature and the presence of metal ions, which can inhibit cell growth and metabolism. Therefore, enhancing microbial tolerance to those unfavorable growth parameters may help to improve pyruvate yield.

DETAILED DESCRIPTION

The goal of the present invention is to provide a genetically engineered *Torulopsis glabrata* (CCTCC No: M202019) with high levels of extracellular pyruvate production, which over-expresses CutA encoding stress protein.

The nucleotide sequence of CutA is set forth in SEQ ID NO: 2 as follows:

```
ATGATCATCG TTTACACTAC TTTCCCAGAC TGGGAATCTG CTGAAAAGGT TGTTAAGACT    60

TTGTTGAAGG AAAGATTGAT CGCTTGTGCT AACTTGAGAG AACACAGAGC TTTCTACTGG   120

TGGGAAGGTA AGATCGAAGA AGACAAGGAA GTTGGTGCTA TCTTGAAGAC TAGAGAAGAC   180

TTGTGGGAAG AATTGAAGGA AAGAATCAAG GAATTGCACC CATACGACGT TCCAGCTATC   240

ATCAGAATCG ACGTTGACGA CGTTAACGAA GACTACTTGA AGTGGTTGAT CGAAGAAACT   300

AAGAAGTAAG                                                          310
```

There are two methods to construct the genetically engineered strain.

One of the methods for constructing the genetically engineered strain comprises the following steps:

(1) Optimizing the CutA derived from *Pyrococcus horikoshii* (SEQ ID NO:1) to obtain SEQ ID NO:2 with codons adapted for usage in *T. glabrata*. A codon adaptation tool, Jcat (http://www.jcat.de), was used to substitute synonymous codons of the CutA sequence of *Pyrococcus horikoshii* to optimize the gene for heterologous expression in *T. glabrata*.

The nucleotide sequence of SEQ ID NO:1 is as follows:

```
ATGATAATAG TTTACACGAC TTTTCCGGAC TGGGAGAGTG CTGAGAAAGT TGTGAAAACT    60

CTTTTAAAAG AGAGGTTGAT TGCATGCGCA AATTTAAGGG AGCACAGGGC CTTTTACTGG   120

TGGGAAGGTA AGATCGAGGA AGATAAAGAA GTTGGAGCTA TCCTTAAAAC TAGGGAAGAT   180

CTGTGGGAAG AACTTAAGGA AAGGATAAAG GAGCTTCATC CTTACGATGT TCCGGCCATA   240

ATCAGGATTG ACGTTGATGA TGTTAACGAG GATTACCTCA AATGGTTAAT TGAAGAGACG   300

AAAAAATGAG                                                          310
```

(2) Constructing a recombinant expression plasmid: synthesize SEQ ID NO:2 by total chemical synthesis; digest the CutA and the plasmid pRS306TEF1 (EUROSARF, Frankfurt, Germany) at the same time using restriction enzyme BamHI and EcoRI, and ligate the digested fragments to obtain a recombinant expression plasmid pRS306TEF1-CutA;

(3) Transforming the recombinant expression plasmid pRS306TEF1-CutA into *T. glabrata* (CCTCC No: M202019) ΔURA3 (a *T. glabrata* (CCTCC No: M202019) strain with URA3 gene being disrupted (Zhou, J., et al. (2009). "A reusable method for construction of non-marker large fragment deletion yeast auxotroph strains: A practice in *Torulopsis glabrata*." Journal of Microbiological Methods 76(1): 70-74) by electroporation method, and screening for positive transformants *T. glabrata* Q1 with YNB medium. Since *T. glabrata* ΔURA3 is inable to synthesize uracil itself, it can not grow on YNB medium without exogenous uracil. Only positive transformant cells with plasmid pRS306TEF1 can synthesize uracil, and therefore is selected to grow on YNB medium without added uracil.

The other method for constructing the genetically engineered strain comprises the following steps:

(1) Optimizing the CutA derived from *Pyrococcus horikoshii* (SEQ ID NO:1) to obtain SEQ ID NO:2;

(2) Constructing a recombinant expression plasmid: synthesize SEQ ID NO:2 by total chemical synthesis; digest the CutA and the plasmid pRS306TEF1 at the same time using restriction enzyme BamHI and EcoRI, and ligate the digested fragments to obtain a recombinant expression plasmid pRS306TEF1-CutA; synthesize promoter sequence (SEQ ID NO:5) of the gene encoding heat shock protein HSP150 derived from *Saccharomyces cerevisae* by total chemical synthesis; digest the promoter sequence and the plasmid pRS306TEF1-CutA at the same time using restriction enzyme SacI and XhoI and connect the digested fragments to obtain a recombinant expression plasmid pRS306-HSP150-CutA;

(3) Transforming the recombinant expression plasmid pRS306HSP150-CutA into *T. glabrata* (CCTCC No: M202019) ΔURA3 by electroporation method, and screening positive transformants *T. glabrata* Q2 with YNB medium.

The genetically engineered strain containing the recombinant expression plasmid is inoculated into a 250 mL flask containing 25 mL seed culture medium, and cultured at 28° C., 200 rpm for 24 hours. The cultured cells were inoculated into 3 L fermentor containing 1.5 L medium with an inoculum size of 10% (v/v), and cultured at 30° C., 400 rpm with an aeration rate of 4 vvm. pH and DO were maintained by feeding 8 mol·L$^{-1}$ NaOH and 2 mol·L$^{-1}$ HCl with automatic pump.

Compared with a control group without expressing CutA, the extracellular concentration of pyruvate of the recombinant strain *T. glabrata* Q1 expressing CutA at 33° C. or 36° C.; the biomass increased 12.4% and 20.7% respectively; the extracellular concentration of pyruvate of the recombinant strain *T. glabrata* Q1 increased from 56.8 g/L to 74.2 g/L.

The present invention provides a method for enhancing temperature tolerance of *T. glabrata* and extracellular concentration of pyruvate by overexpressing the optimized CutA gene. The optimum growth temperature of *T. glabrata* was also increased.

The nucleotide sequence of SEQ ID NO:5 is as follows:

```
   1 acggtgaaag gtataacagc gagaccgaat gaggtccggt actctgttgt gccaccatcc
  61 attttagagc ttggagttaa agttgcccag ggttcaggtg gagcgtacgc agttagcgca
 121 atactactta atagagatgc tagaaatgct ttcttgtaat gcatattggg gcggtgttca
 181 cttcttcagt aagttgtata gaattaaaaa atcgagacta aacagaaatt tcgaaacaag
 241 aagataagta tatgtataca agttatttta ctctttttaac tgttttcgtt tccccactct
 301 ttcgcaaaaa gaataatttt gtgagtcaaa acagtcgaat tttcttgcac aaaaagtcga
 361 tattcttttg tgactctgtg taacttactt tctacagctt ttgttactcc acttctctta
 421 tatataccca atgattcact cgtaatatat cagaggaacg ttagaatttc tgtattttct
 481 caggaatcct acaaaattag aggtgaaatt gatcaggtta aggagcagaa gcccactata
 541 taagtaagat gatatcaagc ctagttggat gccttcagga acggcaaata ggatatgtga
 601 gcttggcaaa ggggtttttga tagagtaaca atagatcctt gctagccaat gcgacgttcc
 661 tctgtagttt ttaccacagt tttacttaat ttcgtgcttt gtccctttttt ggcaaaaaag
 721 tcggataatg tcttcactat atttgtgttt tcgtctttta ggaaaagcgt actttagtaa
 781 actacaaatt tgagctgagc taatttcgga ttagtaaaag atgcaaggaa cagtaaaaat
 841 taaaatagcg attgaccgaa atcagtccaa aaattactac aacaagcaaa tccaattaaa
 901 aacagtaaaa tactttaagt gcatttaccg ttacgaacaa catatgtcct agttagtata
 961 gtagtctact aagtagcaaa aaagtagaaa ctctgtcact ataccagcca tcagttcata
1021 gtaaaacagt aaaaattgta aaaacaagca aaaaaaaaac aagaaggaac aaatgcacca
1081 aactgttgat ctattctgca aaaaaagta tggtaaattt tttccattat cctggccgct
1141 aatccatatg gaggtgaact tagaacttgc acaaggatgc gatgaatgat aggctttgtg
```

-continued

```
1201 ctataattaa tgcaggcagg tccgccatgt ccaacacgtt gctggccgca aaacgagtca 1261 atctcactgc tttgccacgc tcatttctcc cccttctgc ccaattaggc gaccctcaca 1321 atgcacatac acatttccca cctctattgg aaggggccgt aaatggtaat tcttgggagt 1381 tattcatatt aagtgatctt actatttcct atttcggaaa ttattaaaga caaaaaagct 1441 cattaatggc tttccgtctg tagtgataag tcgccaactc agcctaattt ttcatttctt 1501 taccagatca ggaaaactaa tagtacaaat gagtgttttc tcaagcggaa caccacattt 1561 tgagctaaat ttagattttg gtcaaaataa gaaagatcct
```

EXAMPLES

Figure 1:
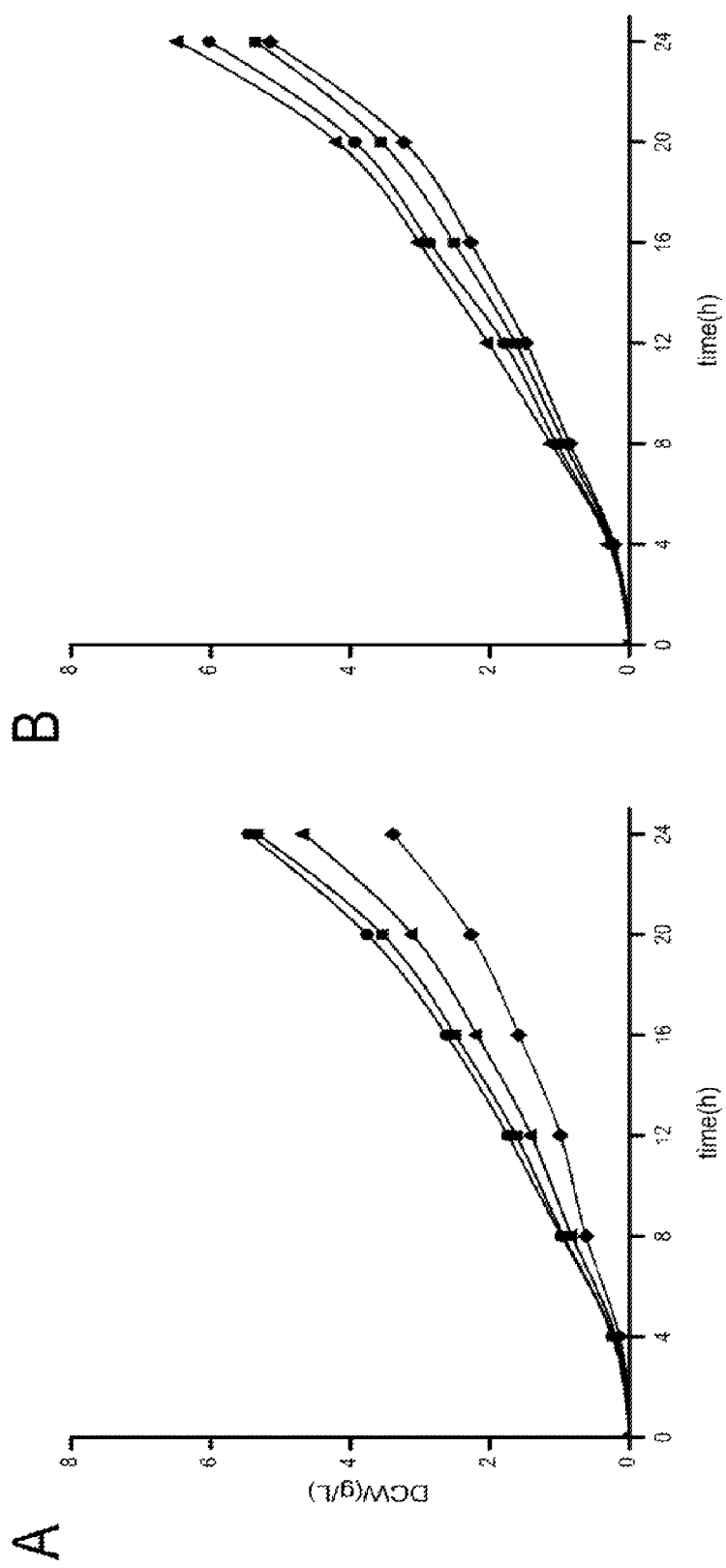
FIG. 1. Effects of expressing CutA on temperature tolerance of T. glabrata. A, cell growth at different temperatures for T. glabrata C. ■: 30° C., •: 33° C., ▲: 36° C., ♦: 39° C.; B, cell growth at different temperatures for T. glabrata Q1. ■: 30° C., •: 33° C., ▲: 36° C., ♦: 39° C.

Materials and Methods:

YPD medium: 5 g·L$^{-1}$ yeast extract, 10 g·L$^{-1}$ peptone, 20 g·L$^{-1}$ dextrose. To make solid medium, add 20 g·L$^{-1}$ Agar.

YNB medium: 20 g·L$^{-1}$ dextrose, 1.7 g·L$^{-1}$ yeast nitrogen base, and 5 g·L$^{-1}$ (NH$_4$)$_2$SO$_4$, adjust pH to 5.0 with 2 mol·L$^{-1}$ NaOH. To make solid medium, add 20 g·L$^{-1}$ Agar.

Seed medium: 20 g·L$^{-1}$ glucose, 10 g·L$^{-1}$ peptone, 1 g·L$^{-1}$ KH$_2$PO$_4$, 0.5 g·L$^{-1}$ MgSO$_4$·7H$_2$O, adjust pH to 5.5 with HCl. To make solid medium, add 20 g·L$^{-1}$ agar. The sterilization was performed at 115° C. for 15 minutes.

Fermentation medium: 100 g·L$^{-1}$ glucose, 7 g·L$^{-1}$ NH$_4$Cl, 5 g·L$^{-1}$ KH$_2$PO$_4$, 0.8 g·L$^{-1}$ MgSO$_4$·7H$_2$O, 6 g·L$^{-1}$ Sodium Acetate, 4×10$^{-3}$ g·L$^{-1}$ Nicotinic acid, 30×10$^{-6}$ g·L$^{-1}$ Thiamin hydrochloride, 100×10$^{-6}$ g·L$^{-1}$ Niacin Pyridoxine, 10×10$^{-6}$ g·L$^{-1}$ Biotin, 50×10$^{-6}$ g·L$^{-1}$ Riboflavin. The vitamins were filtrated for sterilization.

The Torulopsis glabrata was obtained from China Center for Type Culture Collection (CCTCC) with CCTCC No: M202019, which is located at Wuhan University, Luojia Shan, Wuhan, Hubei, 430072.

Determination of extracellular keto acid concentration: fermentation samples were centrifuged at 12000 g for 5 minutes. The supernatant was diluted 50 times with ultra-pure water, and keto acid concentration of the sample was determined using HPLC.

Determination of intercellular keto acid concentration: cells were collected by centrifugation, and washed by 0.9% physiological saline. Cell were resuspended in 10 mL buffer solution containing 0.1 mol·L$^{-1}$ KH$_2$PO$_4$—K$_2$HPO$_4$, 1 mmol·L$^{-1}$ EDTA, 0.01 mmol·L$^{-1}$ DTT (pH 7.5). After addition of one volume of acid-washed quartz sand, cells were disrupted by a vortex mixer for 5 minutes, and centrifuged at 13,000 g for 10 minutes to remove the precipitation. 5 ml supernatant was filtered through a membrane with a pore size 0.22 nm. The concentration of keto acid in the supernatant was then measured using HPLC.

Conditions for HPLC analysis: pyruvate was simultaneously determined by HPLC (Agilent 1200 series, Santa Clara, Calif.) with a Aminex HPX-87H ion exchange column (300 mm×7.8 mm; Bio-Rad Laboratories Inc., Hercules, Calif.). The mobile phase was 5 mmol·L$^{-1}$ sulfuric acid in distilled, de-ionized water filtered through a 0.22 lam pore size membrane. The mobile phase flow rate was 0.6 mL·min$^{-1}$ The column temperature was maintained at 35° C., and the injection volume was 10 μL. The pyruvate was detected by UV (wavelength at 210 nm) detector.

Transformation of Torulopsis glabrata: A freshly grown single colony of T. glabrata ΔURA3 cells were transferred into liquid YPD medium and cultured at 28° C., 200 rpm overnight. The T. glabrata ΔURA3 cells were transferred into new liquid YPD medium by an inoculum size of 10% (v/v), cultured at 28° C., 200 rpm until the OD$_{600}$=1.2. The cells were collected by centrifugation, and resuspended at 8×10$^8$ cells/mL in 8 mL buffer solution (100 mmol·L$^{-1}$ LiAc, 10 mmol·L$^{-1}$ DTT, 0.6 mol·L$^{-1}$ sorbitol 10 mmol·L$^{-1}$ Tris-HCL, pH=7.5) and incubated at 30° C. for 30 minutes. Collect cells again by centrifugation and wash the cells by ice-chilled 5 mL 1 mol·L$^{-1}$ sorbitol solution three times, and resuspend cells to the concentration of 10$^{10}$ cell mL$^{-1}$ in the sorbitol solution. 1 μg purified recombinant plasmid pRS306TEF1-CutA was added to the cell suspension, incubated on ice for 5 min, and transferred to a ice-chilled 0.2-cm electric rotor. The electroporation shock was performed at 2.5 KV, 25 μF, 200Ω, and 1 mL ice-chilled 1 M sorbitol solution was immediately added afterwards. The mixture was incubated at room temperature for 1 hour. 0.2 mL cells, which have been electrically shocked, were spread on the selective culture plates containing YNB medium, and cultured at 28° C. for 96-144 hour. The YNB medium is a basic medium containing no uracil and is used as a selective medium. The T. glabrata ΔURA3 host cells lacks a functional URA3 gene, therefore unable to grow on YNB media. The plasmid pRS306TEF1 harbors a URA3 gene, enabling positive transformants to grow on YNB media without exogenous uracil. The sequence of pRS306TEF1 can be find in the this references (Sikorski, R. S. and P. Hieter (1989). "A system of shuttle vectors and yeast host strains designed for efficient manipulation of DNA in Saccharomyces cerevisiae." Genetics 122(1): 19-27). The heterologous expression of CutA was verified by PCR using primer P1/P2 (Table 1) and genomic DNAs of recombinant T. glabrata cells. The recombinant strain expressing CutA was named T. glabrata Q1, while the recombinant strain expressing control plasmid pRS306TEF1 was named T. glabrata C.

The promoter sequence (SEQ ID NO:5) of the gene encoding heat shock protein HSP150 (GeneID: 853281) derived from Saccharomyces cerevisae was synthesized by total chemical synthesis. Digest the HSP150 promoter sequence and the plasmid pRS306TEF1-CutA at the same time using restriction enzyme SacI and XhoI to replace promoter TEF1 in plasmid pRS306TEF1, and ligate the digested fragments to obtain a recombinant expression plasmid pRS306-HSP150-CutA, where CutA gene is under control of HSP150 promoter. Transform the recombinant expression plasmid pRS306-HSP150-CutA into *T. glabrata* (CCTCC No: M202019) ura3 by electroporation method, and screen positive transformants *T. glabrata* Q2 with YNB medium. The heterologous expression was verified by PCR using primer P1/P2 (Table 1) and genome of original *T. glabrata*. The recombinant strain expressing CutA was named *T. glabrata* Q2.

TABLE 1

Primer sequence

| Primers | Primer sequence (5'-3') |
|---|---|
| P1 (SEQ ID NO: 3) | CTTTCCCAGACTGGGAATCTG |
| P2 (SEQ ID NO: 4) | TTAGTGGTGGTGGTGGTGG |

Example 1

Comparison of Cell Growth of Recombinant Strain *T. glabrata* Q1 and *T. glabrata* C Under Different Temperatures Freshly grown single colonies of *T. glabrata* C and *T. glabrata* Q1 were transferred into 250 mL flasks containing 25 mL liquid YPD medium and cultured at different temperatures: 30° C., 33° C., 36° C. and 39° C., 200 rpm. Dry cell weight (DCW) was measured every 4 hours (FIG. 1).

As it was shown in FIG. 1 that when the strains were cultured at 30° C., there was no obvious difference between cell growth of *T. glabrata* C and *T. glabrata* Q1. When the strains were cultured at 36° C. and 39° C., cell growth of *T. glabrata* C was strongly inhibited and its maximum DCW dropped to 87.4% and 63.6% compared with that obtained at 30° C. When the strains were cultured at 33° C. and 36° C., cell growth of *T. glabrata* Q1 was promoted and its maximum DCW increased to 112.4% and 120.7% compared with that obtained at 30° C. However, cell growth of *T. glabrata* Q1 was also slightly inhibited at 39° C. and the maximum DCW dropped to 96.2% compared with that obtained at 30° C.

Example 2

Temperature-Induced Regulation of CutA Heterologous Expression

To verify the effects of CutA over-expression on temperature tolerance of *T. glabrata*, freshly grown single colonies of *T. glabrata* C and *T. glabrata* Q2 were transferred into 250 mL flask containing 25 mL liquid YPD medium and cultured at 30° C., 200 rpm for 8 hours. Afterwards, the culture temperature was increased to 37° C. to induce the expression of CutA for 16 hours in *T. glabrata* Q2. Dry cell weight (DCW) was measured every 4 hours (FIG. 2).

Figure 2:
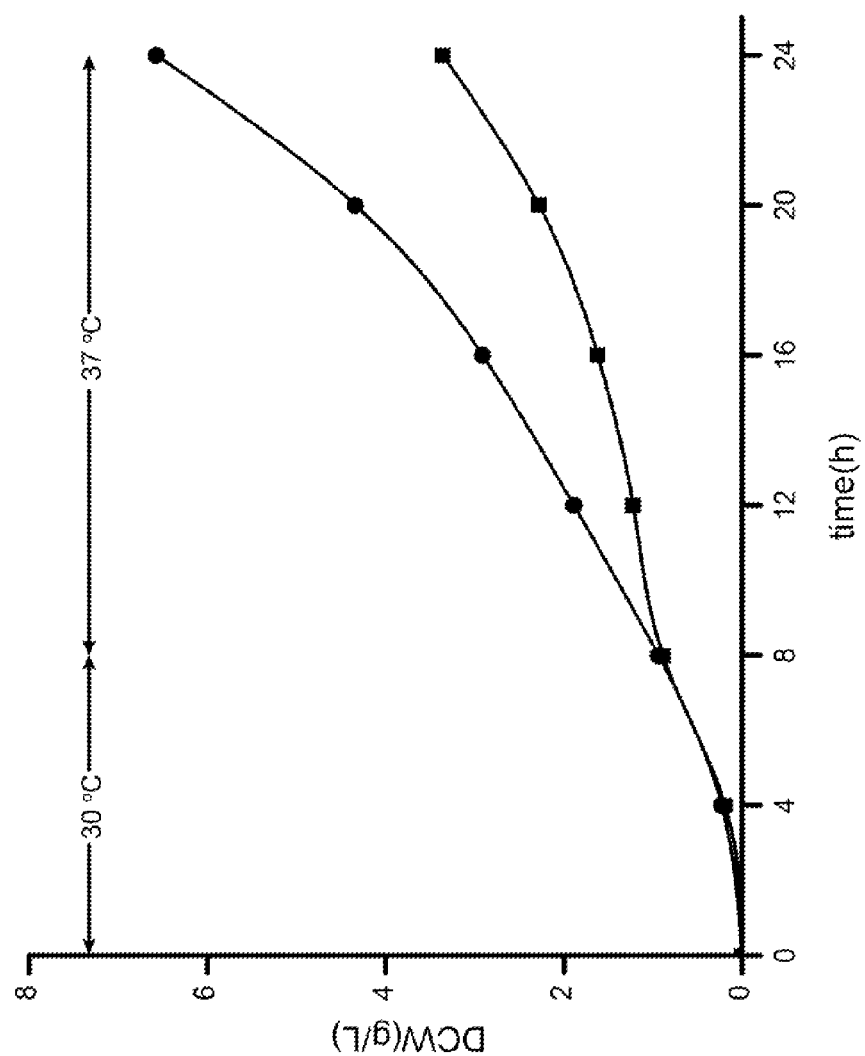
FIG. 2. Temperature-induced regulation of CutA heterologous expression. T. •: glabrata Q1, ■: T. glabrata C.

As shown in FIG. 2, when the strains were cultured at 30° C., there was no obvious difference between cell growth of *T. glabrata* C and *T. glabrata* Q2. However, when the strains were cultured at 37° C., the cell growth of *T. glabrata* C was strongly inhibited while the cell growth of *T. glabrata* Q2 was increased.

Example 3

Effects of High Temperature on Pyruvate Synthesis by Recombinant Strains

Figure 3:
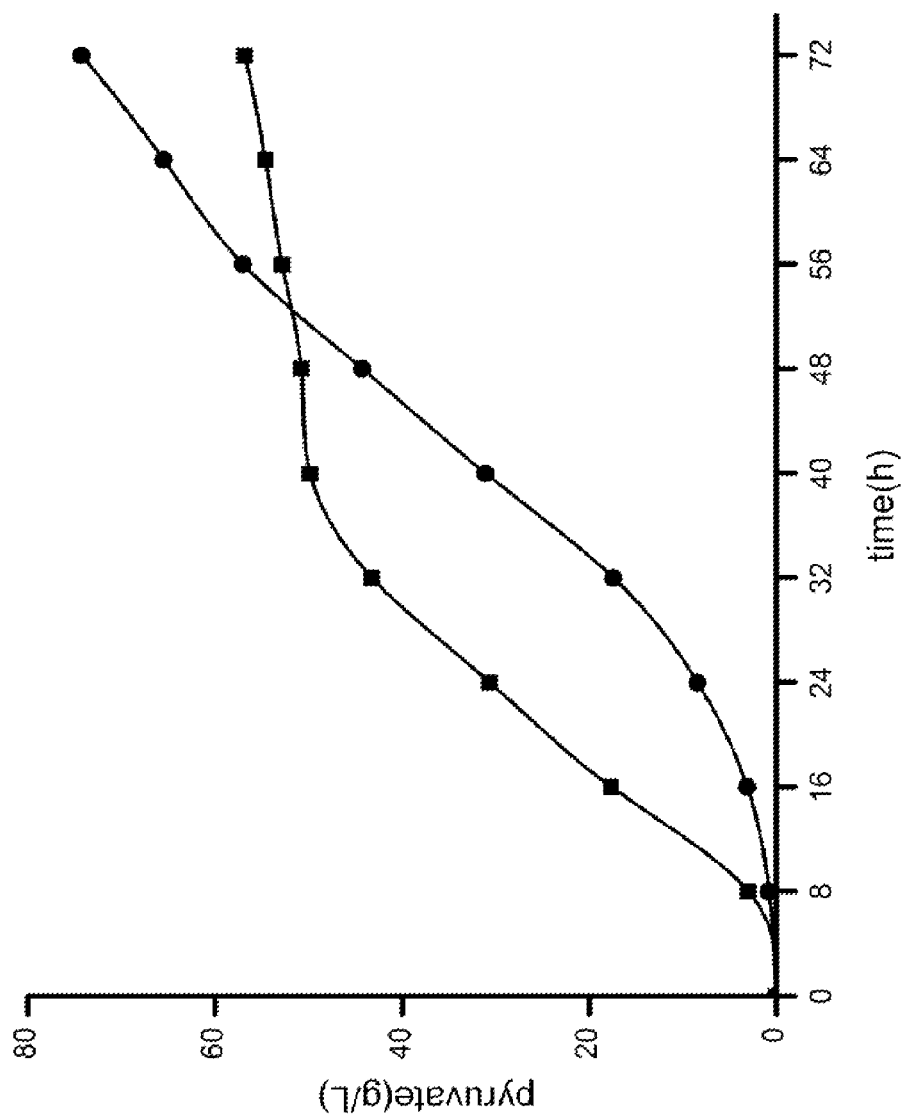
FIG. 3. Effects of high temperature on pyruvate production in T. glabrata strains; ■: T. glabrata C; •: T. glabrata Q1.

Fresh *T. glabrata* Q1 cultures were transferred from solid slant to 500-mL flasks containing 50 mL liquid YPD medium and cultured at 30° C., 200 rpm for 24 hours. The cultured cells were inoculated into fermentation medium with an inoculum size of 10% (v/v), and cultured at 36° C., 200 rpm for 72 hours. *T. glabrata* C cells were inoculated at a rate of 10% (v/v), and was cultured at 30° C., 200 rpm for 72 hours. The comparison of extracellular pyruvate levels of *T. glabrata* C and Q1 was made under their respective optimum culture temperatures (30° C. for *T. glabrata* C and 36° C. for *T. glabrata* Q1). Extracellular concentration of pyruvic acid in the fermentation medium was measured as described above. As shown in FIG. 3, compared with *T. glabrata* C, extracellular concentration of pyruvate of *T. glabrata* Q1 increased from 56.8 g·L$^{-1}$ to 74.2 g·L$^{-1}$.

* * *

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A genetically engineered *Torulopsis glabrata* (*T. glabrata*) strain with enhanced extracellular secretion of pyruvic acid as compared to its parent *T. glabrata* strain, wherein said *T. glabrata* strain is obtained from China Center for Type Culture Collection with CCTCC No: M202019 and is genetcay engineered to over-express a CutA gene encoding a stress protein that comprises the nucleotide sequence of SEQ. ID NO:2.

2. A method of constructing the genetically engineered *T. glabrata* strain of claim 1, comprising the steps of:
   1) Optimizing a CutA gene derived from *Pyrococcus horikoshii* (SEQ ID NO:1) to obtain SEQ ID NO:2, wherein said CutA gene of SEQ ID NO:2 is adapted to the codon usage preference of *T. glabrata* cells;
   2) Constructing a recombinant plasmid expressing said optimized CutA gene;
   3) Transforming said recombinant plasmid expressing said optimized CutA into *T. glabrata* (CCTCC No: M202019) ΔURA3; and
   4) Screening positive transformants with said recombinant plasmid expressing said optimized CutA.

3. The method of claim 2, wherein said recombinant plasmid expressing said optimized CutA is constructed by digesting plasmid pRS306TEF1 and chemically synthesized SEQ ID NO:2 with restriction enzymes BamHI and EcoRI, and ligating the digested fragments.

4. The method of claim 2, wherein said recombinant plasmid expressing said optimized CutA is constructed to have a heat-induced promoter for controlling CutA expression.

5. The method of claim 4, wherein said heat-induced promoter is the promoter sequence (SEQ ID NO:5) for heat shock protein HSP150 of *Saccharomyces cerevisae*.

6. The method of claim 4, wherein said recombinant plasmid expressing said optimized CutA under control of said heat-induced promoter is constructed by:
   1) synthesizing an optimized CutA of SEQ ID NO:2 by total chemical synthesis;
   2) digesting said optimized CutA and the plasmid pRS306TEF1 at the same time using restriction enzyme BamHI and EcoRI;
   3) ligating the digested fragments to obtain a recombinant expression plasmid pRS306TEF1-CutA;
   4) synthesizing a promoter sequence (SEQ ID NO:5) of the gene encoding heat shock protein HSP150 of *Saccharomyces cerevisae* by total chemical synthesis;
   5) digesting said promoter sequence and said recombinant expression plasmid pRS306TEF1-CutA at the same time using restriction enzyme SacI and XhoI; and
   6) ligating the above digested fragments to obtain said recombinant plasmid expressing said optimized CutA under control of said heat-induced promoter.

7. A method of producing pyruvate using the genetically engineered *T. glabrata* strain of claim 1, comprising the steps of:
   1) inoculating said genetically engineered *T. glabrata* strain containing the CutA-expressing plasmid from a solid slant to a 250 mL flask containing 25 mL seed culture medium;
   2) culturing at 28° C., 200 rpm for 24 hours;
   3) inoculating the cultured cells into a 3 L fermentor containing 1.5 L medium with an inoculum size of 10% (v/v);
   4) culturing at 30° C., 400 rpm with an aeration rate of 4 vvm and maintaining pH by feeding 8 mol·L$^{-1}$ NaOH and 2 mol·L$^{-1}$ HCl with automatic pump; and
   5) collecting pyruvate from the supernatant of the fermentation broth.

8. The method of claim 7, wherein said seed medium consists of 20 g·L$^{-1}$ glucose, 10 g·L$^{-1}$ peptone, 1 g·L$^{-1}$ KH$_2$PO$_4$, 0.5 g·L$^{-1}$ MgSO$_4$·7H$_2$O, pH 5.5.

9. The method of claim 7, wherein said fermentation medium consists of 100 g·L$^{-1}$ glucose, 7 g·L$^{-1}$ NH$_4$Cl, 5 g·L$^{-1}$ KH$_2$PO$_4$, 0.8 g·L$^{-1}$ MgSO$_4$.7H$_2$O, 6 g·L$^{-1}$ Sodium Acetate, 4×10$^{-3}$ g·L$^{-1}$ Nicotinic acid, 30×10$^{-6}$ g·L$^{-1}$ Thiamin hydrochloride, 100×10$^{-6}$ g·L$^{-1}$ Niacin Pyridoxine, 10×10$^{-6}$ g·L$^{-1}$ Biotin, 50×10$^{-6}$ g·L$^{-1}$ Riboflavin, pH 5.0, wherein Nicotinic acid, Thiamin hydrochlorid, Niacin Pyridoxine and Biotin are filtrated for sterilization.

* * * * *